(12) United States Patent
Kaal et al.

(10) Patent No.: US 8,002,745 B2
(45) Date of Patent: Aug. 23, 2011

(54) RETRACTABLE SYRINGE WITH PLUNGER DISABLING SYSTEM

(75) Inventors: Joseph Hermes Kaal, Morpeth (AU); Craig Stephen Thorley, Largs (AU); Damien Judd, Heathmont (AU)

(73) Assignee: Unitract Syringe Pty Ltd., West Perth, Western Australia (AU)

( * ) Notice: Subject to any disclaimer, the term of this patent is extended or adjusted under 35 U.S.C. 154(b) by 675 days.

(21) Appl. No.: 10/587,705

(22) PCT Filed: Jan. 28, 2005

(86) PCT No.: PCT/AU2005/000107
§ 371 (c)(1),
(2), (4) Date: Oct. 3, 2006

(87) PCT Pub. No.: WO2005/072801
PCT Pub. Date: Aug. 11, 2005

(65) Prior Publication Data
US 2008/0255513 A1 Oct. 16, 2008

Related U.S. Application Data

(60) Provisional application No. 60/638,623, filed on Dec. 22, 2004.

(30) Foreign Application Priority Data

Jan. 28, 2004 (AU) .............................. 2004900362
Oct. 22, 2004 (AU) .............................. 2004906116

(51) Int. Cl.
*A61M 5/00* (2006.01)
(52) U.S. Cl. .................................................. 604/110

(58) Field of Classification Search .................. 604/110, 604/192, 240
See application file for complete search history.

(56) References Cited

U.S. PATENT DOCUMENTS

| | | | | |
|---|---|---|---|---|
| 5,112,316 A | * | 5/1992 | Venturini | 604/195 |
| 5,169,392 A | * | 12/1992 | Ranford et al. | 604/198 |
| 5,190,526 A | * | 3/1993 | Murray et al. | 604/110 |
| 5,205,824 A | * | 4/1993 | Mazur | 604/110 |
| 5,211,628 A | * | 5/1993 | Marshall | 604/110 |
| 5,211,630 A | | 5/1993 | Schmahmann | |
| 5,279,579 A | * | 1/1994 | D'Amico | 604/192 |

(Continued)

FOREIGN PATENT DOCUMENTS

AU  39180/89 A  2/1991

(Continued)

*Primary Examiner* — Nicholas D Lucchesi
*Assistant Examiner* — Diva Ranade
(74) *Attorney, Agent, or Firm* — LeClairRyan (57) ABSTRACT

A retractable syringe includes a barrel, a collar mounted to the barrel, a retraction spring and a needle mount. The plunger includes a first plunger member and a second plunger member that are releasably coupled to initially compress the spring. The second plunger member further includes a seal to prevent fluid leakage between plunger and barrel. After depression of the plunger to deliver the syringe fluid contents, the first plunger member engages the needle mount with needle attached thereto and is rotatably uncoupled from the second plunger member to allow decompression of the retraction spring, which forces retraction of the first plunger member, needle mount and needle engaged therewith. The first plunger member and the collar include elements that co-operatively disable subsequent depression or withdrawal of the plunger. Following retraction of the first plunger member, the second plunger member and seal prevent refilling and re-use of the syringe.

32 Claims, 11 Drawing Sheets

U.S. PATENT DOCUMENTS

| | | | |
|---|---|---|---|
| 5,328,476 A | 7/1994 | Bidwell | |
| 5,330,430 A * | 7/1994 | Sullivan | 604/134 |
| 5,338,304 A * | 8/1994 | Adams | 604/110 |
| 6,083,199 A * | 7/2000 | Thorley et al. | 604/110 |
| 6,585,702 B1 | 7/2003 | Brunel | |
| 6,716,191 B2 * | 4/2004 | Sergio | 604/110 |
| 6,729,370 B2 * | 5/2004 | Norton et al. | 141/329 |
| 6,840,899 B2 * | 1/2005 | Koga et al. | 600/29 |
| 7,300,416 B2 * | 11/2007 | Botich et al. | 604/110 |
| 7,316,669 B2 * | 1/2008 | Ranalletta | 604/199 |
| 2001/0053886 A1 * | 12/2001 | Caizza | 604/110 |
| 2002/0111588 A1 * | 8/2002 | Restelli | 604/218 |
| 2002/0161340 A1 * | 10/2002 | Sharp | 604/220 |
| 2003/0045838 A1 * | 3/2003 | Woodard et al. | 604/218 |
| 2003/0158525 A1 * | 8/2003 | Thorley et al. | 604/240 |
| 2003/0229314 A1 * | 12/2003 | McWethy et al. | 604/197 |
| 2003/0236501 A1 * | 12/2003 | Donnan et al. | 604/192 |
| 2004/0030294 A1 * | 2/2004 | Mahurkar | 604/192 |
| 2004/0236283 A1 * | 11/2004 | Tang | 604/197 |
| 2005/0049554 A1 * | 3/2005 | Chueh | 604/110 |
| 2005/0054979 A1 * | 3/2005 | Liu | 604/110 |
| 2005/0070854 A1 * | 3/2005 | Wright | 604/197 |
| 2005/0240150 A1 * | 10/2005 | Gordon | 604/110 |
| 2006/0189935 A1 * | 8/2006 | Janek et al. | 604/110 |
| 2006/0235354 A1 * | 10/2006 | Kaal et al. | 604/110 |
| 2007/0043322 A1 * | 2/2007 | Lee et al. | 604/110 |
| 2007/0060885 A1 * | 3/2007 | Wu | 604/110 |
| 2007/0299395 A1 * | 12/2007 | Pelkey et al. | 604/110 |
| 2008/0281266 A1 * | 11/2008 | Walton et al. | 604/110 |
| 2009/0171285 A1 * | 7/2009 | Wang | 604/110 |
| 2009/0216188 A1 * | 8/2009 | Woehr et al. | 604/110 |
| 2009/0312703 A1 * | 12/2009 | Pickhard | 604/110 |
| 2010/0063443 A1 * | 3/2010 | Lin Lee | 604/110 |

FOREIGN PATENT DOCUMENTS

| | | |
|---|---|---|
| EP | 0434008 B1 | 6/1994 |
| GB | 2341804 A | 3/2000 |

\* cited by examiner

RETRACTABLE SYRINGE WITH PLUNGER DISABLING SYSTEM

This application is a national stage application under 35 U.S.C. §371 from PCT Application No. PCT/AU2005/000107, filed Jan. 28, 2005, which claims the priority benefit of Australian Patent Application Nos. 2004900362, filed Jan. 28, 2004 and 2004906116, filed Oct. 22, 2004, and U.S. Provisional Patent Application No. 60/638,623, filed Dec. 22, 2004.

FIELD OF THE INVENTION

This invention relates to a syringe and plunger therefor. More particularly, this invention relates to a permanently retractable, single use syringe where the plunger can be automatically disabled.

BACKGROUND OF THE INVENTION

The practice of sharing syringes without adequate sterilisation between successive users is a major contributor to the transfer of Human Immunodeficiency Virus and Hepatitis with subsequent severe repercussions for the sufferer of such diseases and at a high cost to society of supporting and providing medical attention to those sufferers.

Another significant risk associated with unclean needles and syringes arises from the possibility of inadvertent needlestick injuries. This is particularly a problem for law enforcement officers and paramedics who often encounter users of illegal drugs in their professional activities. Additionally, the habits of illegal drug users are such that dangerous by-products of their activities, such as discarded syringes, are often left in places of public access presenting a risk to the users of areas such as public parks and school grounds.

Used syringes are also dangerous in hospitals, medical centres and surgeries where needlestick injuries may injure doctors, nurses and other health professionals.

A recent development in syringes has been to design syringes where the needle is permanently retractable into the barrel of the syringe.

For example, International Publication WO 01/80930 describes a single-use retractable syringe that is highly effective in preventing syringe re-use by ensuring full depression of the plunger during fluid delivery and by ensuring permanent withdrawal of the needle by the plunger back into the syringe barrel.

In such cases, retraction is facilitated by a spring, which at the end of injection forces the plunger and needle engaged therewith to retract into the barrel automatically.

OBJECT OF THE INVENTION

Although very effective, prior art retractable syringes having spring-driven retraction mechanisms have limitations, particularly associated with higher volume syringes, such as 3, 5 and 10 mL syringe. In this regard, the size of the spring needed to drive retraction of the plunger and needle can be too large to fit into the syringe.

Furthermore, some users do not like the feel associated with gradual compression of the spring as the plunger is depressed, which can prove can provide a disincentive to use a spring-driven retractable syringe.

It is therefore an object of the invention to overcome or alleviate at least one of the deficiencies of the prior art, or at least provide a useful alternative.

SUMMARY OF THE INVENTION

The present invention is therefore broadly directed to a retractable syringe which comprises a spring-driven mechanism to automatically disable the retractable syringe and thereby prevent re-use of the retractable syringe, wherein the spring is retained in an initial compressed state by the plunger until decompression of the spring is required to drive retraction of the plunger and syringe needle engaged therewith.

The present invention is also broadly directed to a plunger suitable for use with the retractable syringe of the invention.

A preferred advantage of the syringe and/or plunger of the invention is that the plunger can retain a relatively large spring in an initial compressed state until decompression is required for retraction of the needle.

Another preferred advantage of the syringe and/or plunger of the invention is that the spring is retained in a compressed state until after delivery of fluid contents of the syringe, without a user having to compress the spring during plunger depression. This provides a smoother "feel" to the user during delivery.

In a first aspect, the invention provides plunger for a retractable syringe having a spring and a needle mount, said plunger comprising a first plunger member and a second plunger member that are releasably engageable to co-operatively maintain said spring in an initial compressed state, arranged so that disengagement of said first plunger member and said second plunger member can facilitate decompression of said spring from an initial compressed state when required to force retraction of said first plunger member and said needle mount when engaged therewith, following depression of said plunger to deliver fluid contents of said syringe.

In a second aspect, the invention provides a retractable syringe comprising a plunger, a barrel, a spring and a needle mount, said plunger comprising a first plunger member and a second plunger member that are releasably engaged to co-operatively maintain said spring in an initial compressed state and are disengageable to facilitate decompression of said spring to force retraction of said first plunger member and said needle mount when engaged therewith following depression of said plunger to deliver fluid contents of said syringe.

Preferably, said syringe further comprises a collar mounted to the barrel that includes one or more projections engageable with said plunger.

The one or more projections may comprise a plurality of pawls, ribs, fingers, fins, nubs or like structures.

The one or more projections may comprise first and second projections that can be slidably located and are movable within respective first and second guide slots in the first plunger member to assist in maintaining a desired alignment of said plunger.

The retractable syringe may further comprise a disabling means that may prevent, minimize or at least reduce the likelihood of subsequent depression and/or withdrawal of said first plunger member following retraction of the first plunger member, needle mount and a needle mounted thereto.

In a preferred form, said collar comprises a plurality of projections that comprise said first and second projections together with third and fourth projections that can co-operate with respective abutments on said first plunger member to form said disabling means.

Preferably, the third and fourth projections are pawls.

Preferably, in use said plurality of projections can bear against said respective abutments on said first plunger member following retraction of said first plunger member to thereby disable subsequent withdrawal and/or depression of said first plunger member.

In a particularly preferred form, the invention provides a retractable syringe comprising:
  (i) a barrel;
  (ii) a collar mounted to the barrel and comprising two ribs and two pawls;
  (iii) a retraction spring;
  (iv) a needle mount located at a needle end of the barrel to which is mounted a needle; and
  (v) a plunger operably located in said barrel and engageable with said needle mount, said plunger comprising:
    (a) a first plunger member having two steps and two ledges; and
    (b) a second plunger member comprising a seal;
wherein the first plunger member and the second plunger member are releasably coupled to co-operatively maintain said spring in an initial compressed state and can subsequently be rotatably uncoupled to facilitate decompression of said spring to force retraction of said first plunger member and said needle mount when engaged therewith following depression of said plunger to deliver fluid contents of said syringe and wherein said two pawls are engageable with respective steps on said first plunger member to co-operably prevent subsequent depression said first plunger member and said two ribs are engageable with respective ledges on said first plunger member to co-operably prevent subsequent withdrawal of said first plunger member following retraction of the needle mount and needle.

In a preferred from, said syringe is arranged so that following retraction of the first plunger member, needle mount and needle, the second plunger member and seal remain at a needle end the barrel thereby preventing, minimizing or reducing the potential for refilling of the syringe and thus preventing, minimizing or reducing the potential for syringe re-use.

Throughout this specification, unless otherwise indicated, "comprise", "comprises" and "comprising" are used inclusively rather than exclusively, so that a stated integer or group of integers may include one or more other non-stated integers or groups of integers.

BRIEF DESCRIPTION OF THE DRAWINGS

Non-limiting embodiments of the invention are described herein with reference to the accompanying drawings in which.

DETAILED DESCRIPTION OF THE INVENTION

Figure 1:
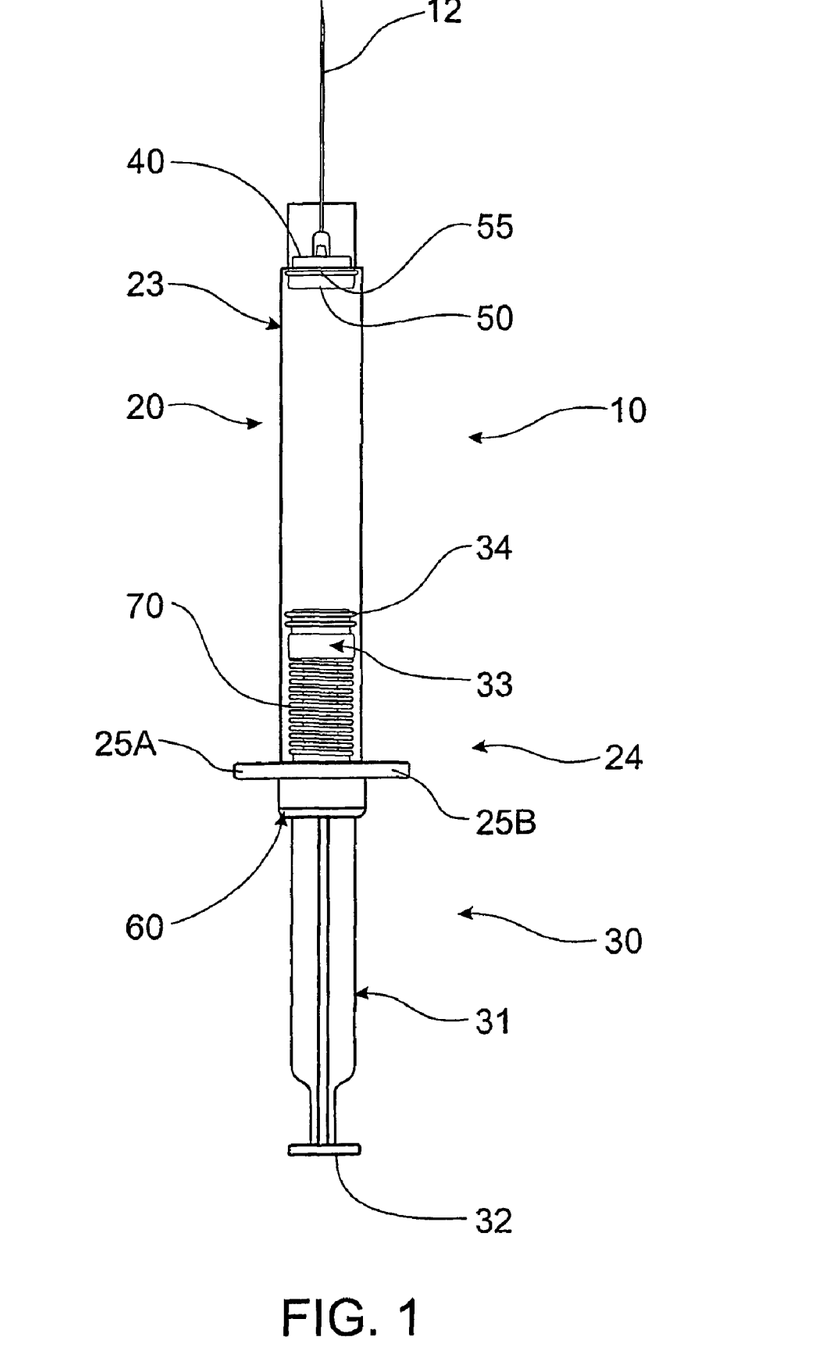
FIG. 1 is a side view of an embodiment of a retractable syringe.

Referring to an embodiment shown in FIG. 1, retractable syringe 10 comprises barrel 20, plunger 30 operably located therein and needle mount 40 with retractable needle 12. Needle mount 40 is mounted at needle end 23 of barrel 20 with barrel insert 50 and O-ring 55. Finger grips 25A, 25B are provided at plunger end 24 of barrel 20, at which end is mounted collar 60. Plunger 30 comprises first plunger member 31 with button 32 operable by a user and second plunger member 33 and seal 34 mounted thereto, releasably coupled to first plunger member 31 to co-operatively maintain spring 70 in a compressed state until required for retraction of needle mount 40 and needle 12.

Figure 2:
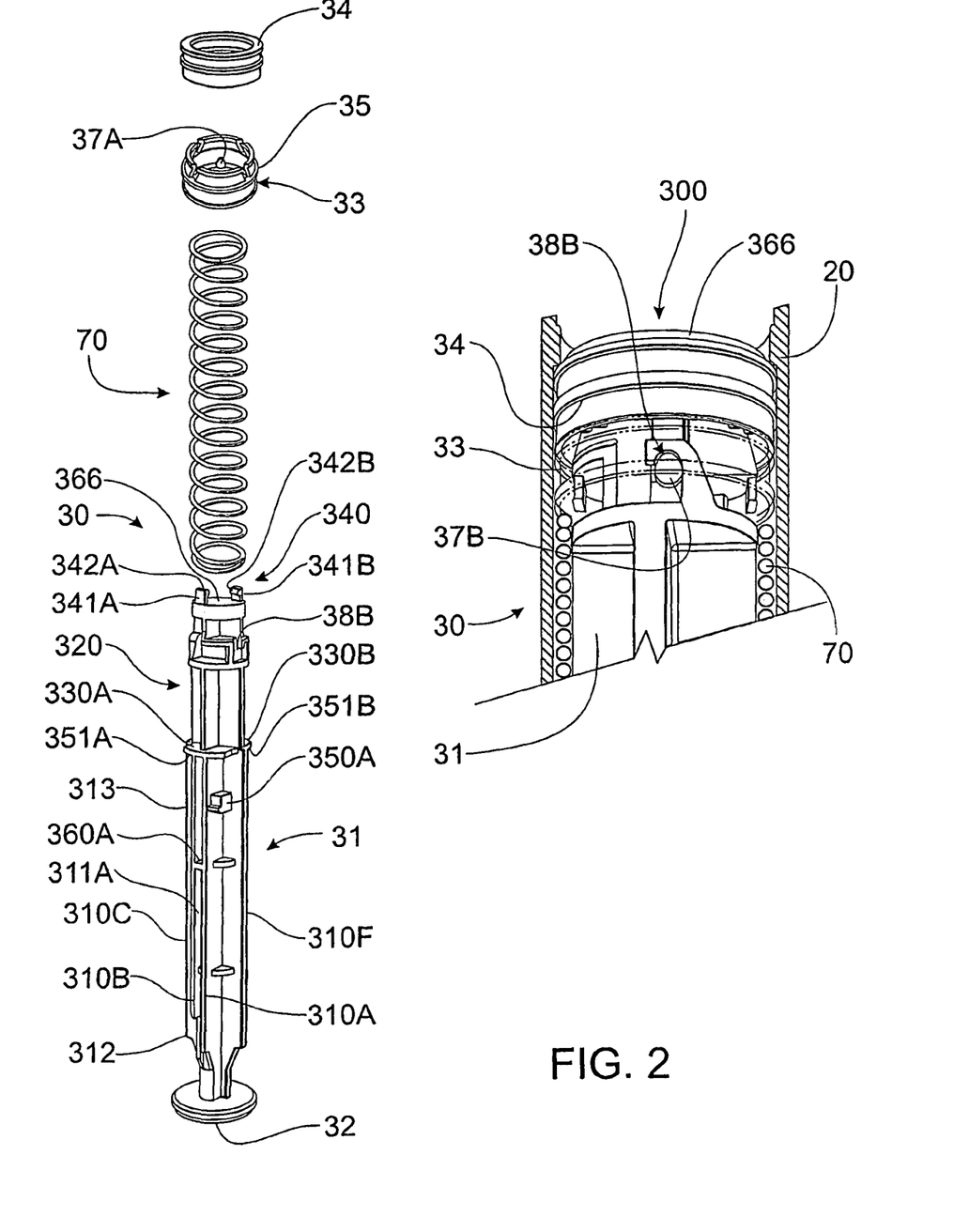
FIG. 2 is a perspective view of an embodiment of a first plunger member, a second plunger member with a seal and a spring with inset showing coupling means of first plunger member and second plunger member.

Referring now to FIG. 2, plunger 30 comprises a first plunger member in the form of plunger rod 31 having button 32 operable by a user, and a second plunger member in the form of seal mount 33. When assembled, seal 34 is mounted to seat 35 in seal mount 33, which seal 34 in use, prevents or minimizes leakage of fluid between plunger 30 and internal wall 21 of barrel 20.

As specifically shown in the inset to FIG. 2, seal mount 33 is mounted to plunger rod 31 by a coupling means 300, which in this embodiment is a bayonet coupling formed between tabs 37A, 37B in seal mount 33 and respective coupling indents 38A, 38B in plunger rod 31. Coupling indents 38A, 38B are configured to allow restricted longitudinal movement (no more than about 1-2 mm) of seal mount 33 relative to plunger rod 31 when mounted thereto.

Plunger rod 31 has a plurality of elongate, parallel vanes 310A, 310B, 310C, 310D (not visible) and 310F extending longitudinally along plunger rod 31. Vanes 310A, 310B define first guide slot 311A having gate 312. Vanes 310B and 310C define retraction space 313. Although not visible in FIG. 2, one embodiment of the invention further comprises vane 310E as shown in FIG. 6C, which together with vane 310D, defines second guide slot 311B, the function of which will be described in more detail hereinafter.

Plunger rod 31 has reduced diameter portion 320 over which spring 70 is loaded, spring 70 bearing against rims 330A, 330B which thus cooperate with seal mount 33 when coupled to plunger rod 31 to maintain spring 70 in a compressed state until retraction of needle mount 40 and needle 12 is required. Spring 70 is shown non-compressed in FIG. 2.

Plunger rod 31 further comprises means 340 for engaging needle mount 40. In this embodiment, means 340 comprises opposed barbed arms 341A, 341B having barb ends 342A, 342B that can engage needle mount 40 at the end of plunger 30 depression, as will be described in more detail hereinafter.

Plunger rod further comprises a plurality of abutments, in this embodiment steps 350A, 350B (not shown) and ledges 351A, 351B, that can co-operate with respective projections on collar 60 to form disabling means 80 to be described in more detail hereinafter.

Figure 3:
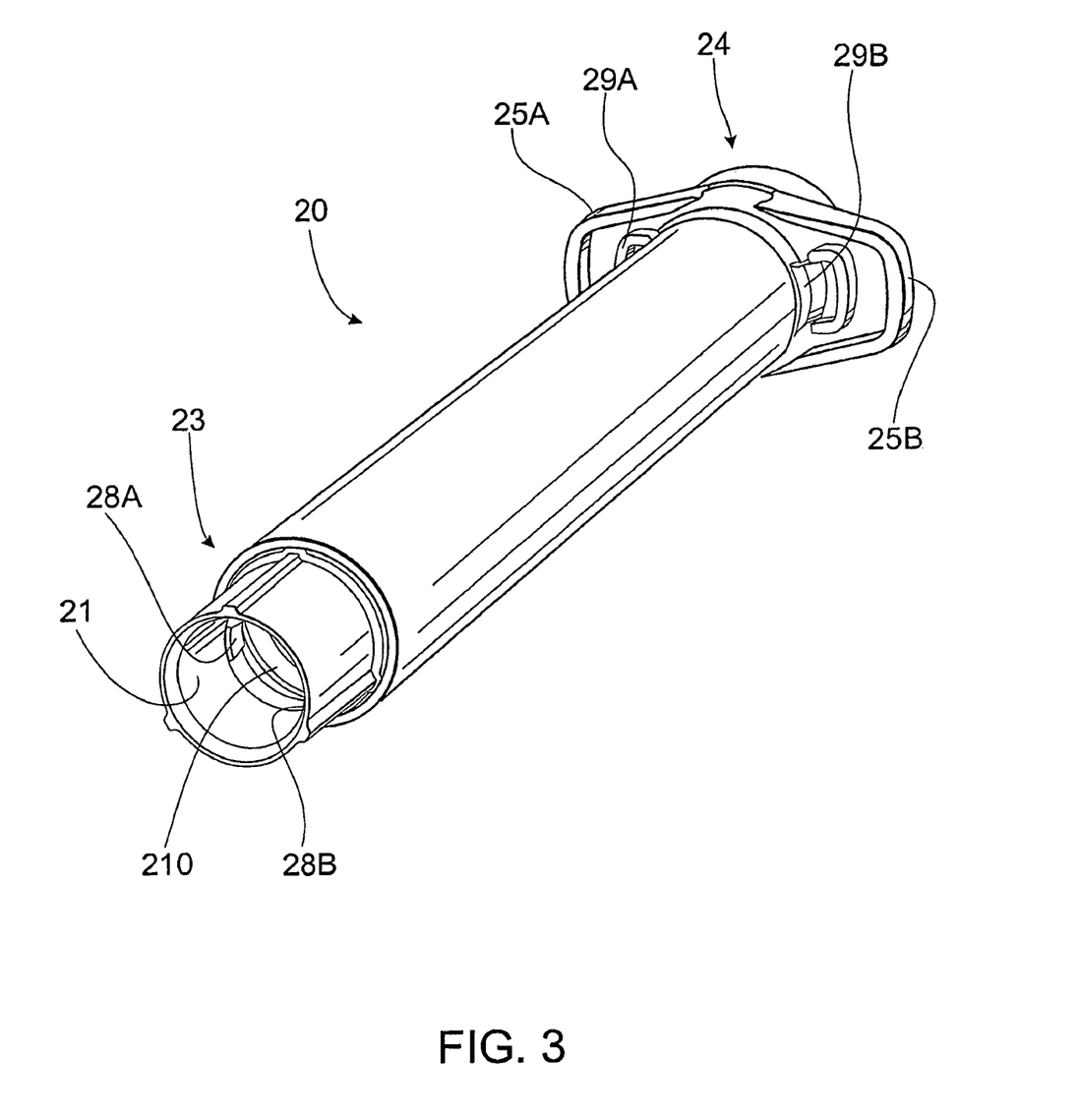
FIG. 3 is a perspective view of an embodiment of a barrel.

Referring to FIG. 3, barrel 20 is adapted so that needle mount 40 and barrel insert 50 can be fitted at needle end 23, while collar 60 can be mounted at plunger end 24. Tapered tabs 28A, 28B (not shown) facilitate mounting and retention of needle mount 40. Barrel 20 also comprises locating slots 29A, 29B at plunger end 24 that facilitate mounting and retention of collar 60 and, at needle end 23, seat 210 for mounting O-ring 55.

Figure 4:
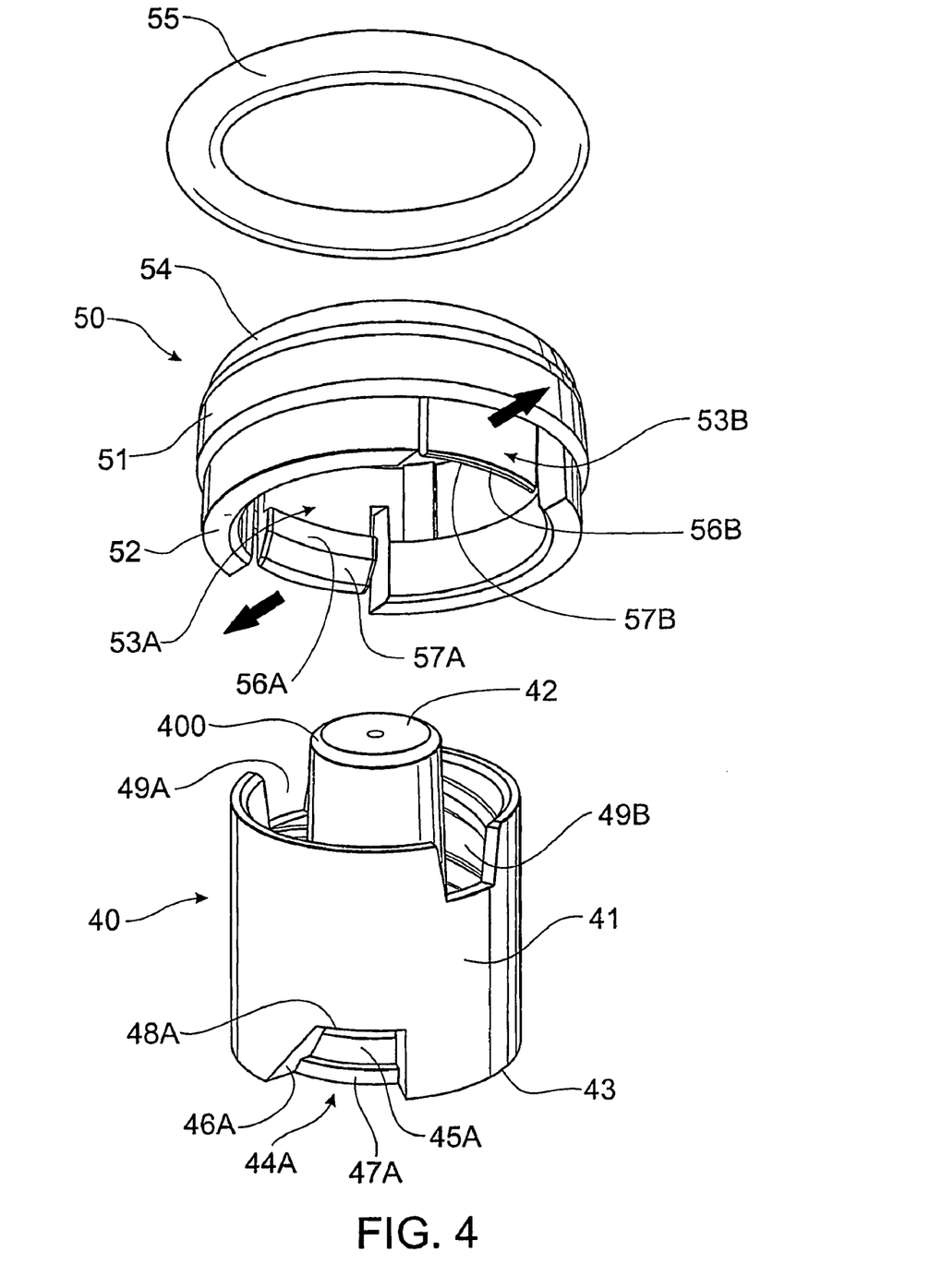
FIG. 4 is a perspective view of an embodiment of a barrel insert, an O-ring and a needle mount.

With reference to FIG. 3 and FIG. 4, barrel insert 50 has annular body 51 with rim 54, base 52 and arms 53A, 53B having respective grips 56A, 56B with angled faces 57A, 57B, O-ring 55 is fitted into seat 210 of barrel 20 to effect a seal between needle mount body 41 and internal wall 21 of barrel 20.

Needle mount 40 comprises body 41 having central bore 42, base rim 43 and plunger-engaging means 44A, 44B (not visible in FIG. 4) that comprise respective barb recesses 45A, 45B, angled faces 46A, 46B, lips 47A, 47B and upper ledges 48A, 48B. Needle mount body 41 further comprises opposed, tapered recesses 49A, 49B that in use are engaged by respective, tapered tabs 28A, 28B on inside wall 21 of barrel 20 to thereby fix needle mount 40 in position at needle end 23 of barrel 20 and limit movement of needle mount 40 toward needle end 23.

When assembled into syringe 10, base rim 43 of needle mount 40 is held by grips 56A, 56B of respective arms 53A, 53B of barrel insert 50, which prevents unwanted movement of needle mount 40 in the direction of plunger end 24 of barrel 20. Preferably, arms 53A, 53B of barrel insert 50 are oriented at approximately 90° relative to respective plunger-engaging portions 44A, 44B of needle mount 40.

Arms 53A, 53B are resiliently deformable in the direction indicated by solid arrows. Radial outward movement of arms 53A, 53B allows release of needle mount 40 for subsequent retraction of needle mount 40 as will be described in more detail hereinafter.

An advantage provided by needle mount 40 is that a user may replace the needle should it become bent or burred, or should the needle gauge be changed (i.e between filling and delivery) without affecting the retraction mechanism.

A feature of needle mount 40 is that it may include whichever type of needle fitting is desired, such as luer taper 400, for example with a luer lock or luer slip, although without limitation thereto.

Figure 5:
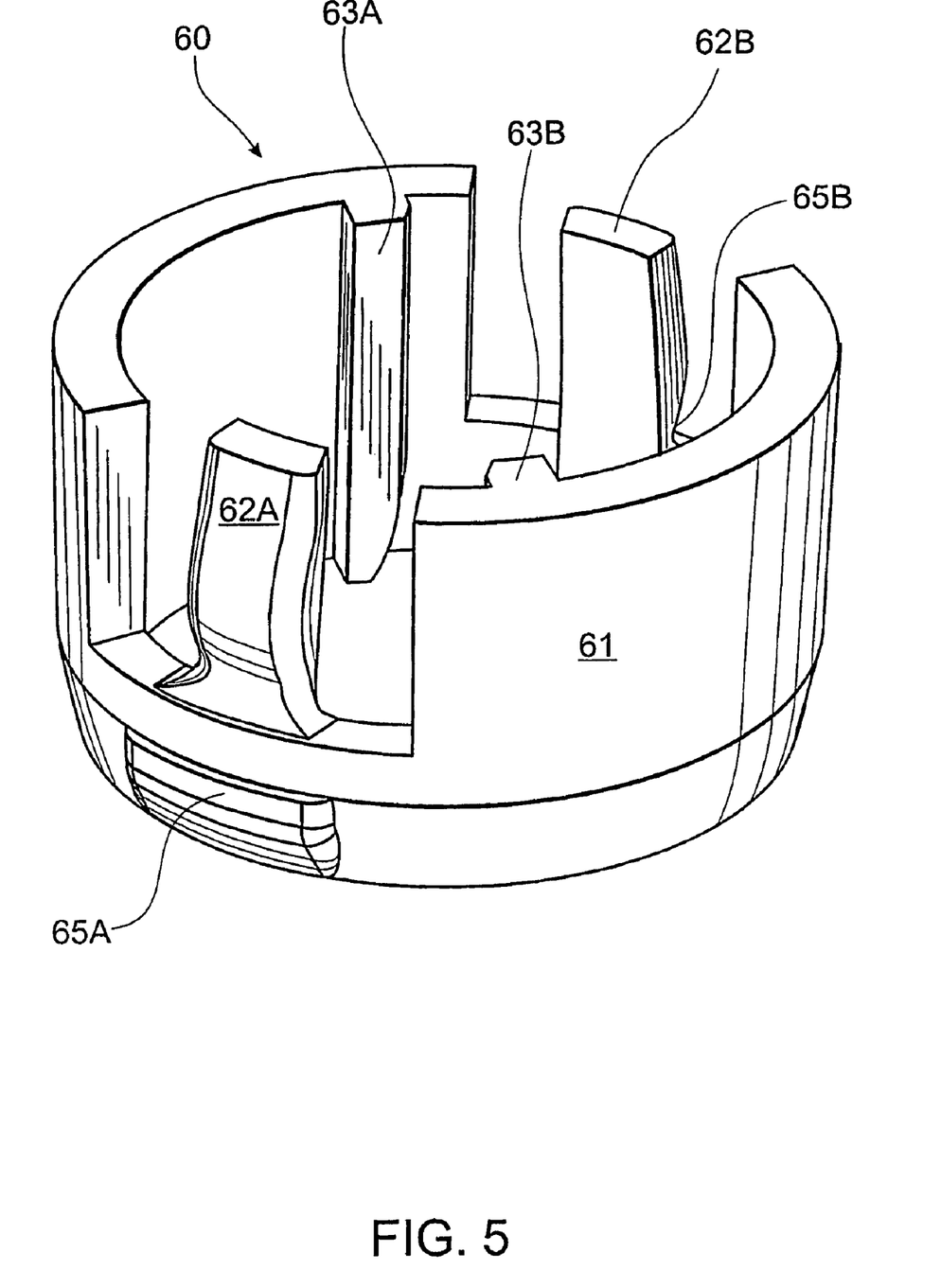
FIG. 5 is a perspective view of an embodiment of a collar.

Referring to FIG. 3 and FIG. 5, barrel 20 comprises locating slots 29A, 29B (slot 29A not visible) in plunger end 24, which facilitate mounting of collar 60. Collar 60 has body 61 with a plurality of projections comprising pawls 62A, 62B and ribs 63A, 63B. Collar 60 further comprises barrel-engaging shoulders 65A, 65B (shoulder 65B not visible) that fit into respective locating slots 29A, 29B (29B not visible) of barrel 20 to thereby mount collar 60 into plunger end 24 of barrel 20.

The operation of an assembled syringe 10 will now be described.

As shown in FIG. 2, plunger 30 is assembled so that first plunger member 31 and second plunger member 33 are releasably coupled by way of coupling means 300 to thereby maintain spring 70 in a compressed state until retraction of needle mount 40 and needle 12 fitted thereto, is required.

Figure 6A:
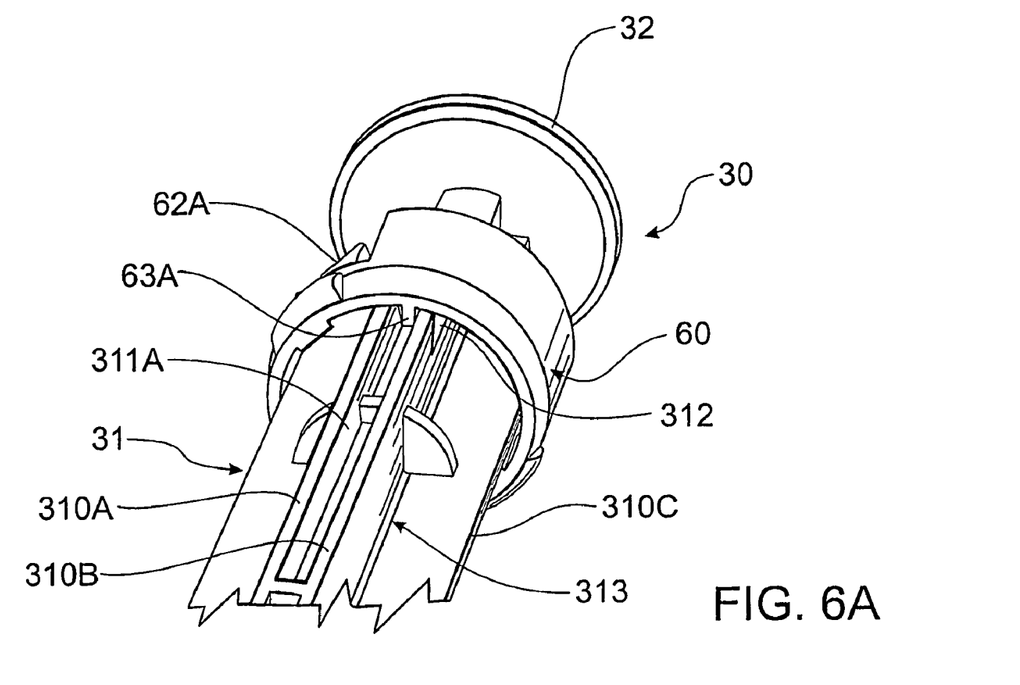
FIG. 6A is a perspective view showing a first collar projection in a first guide slot in a first plunger member during plunger withdrawal.
Figure 6B:
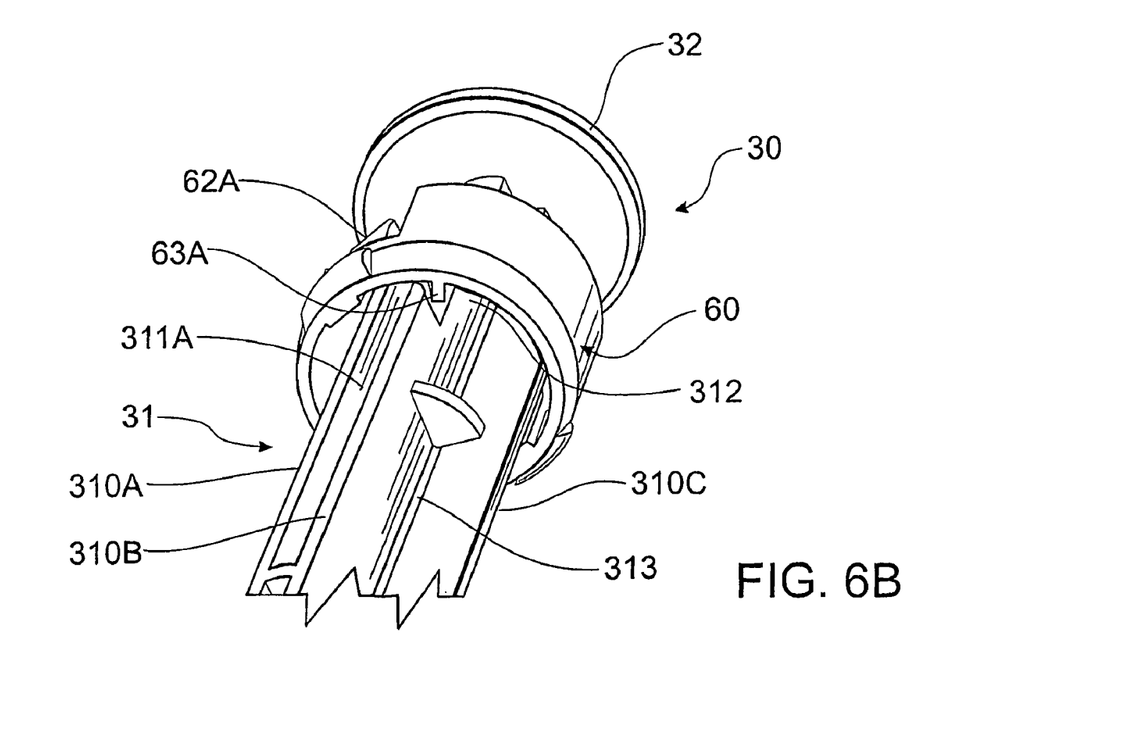
FIG. 6B shows movement of the first collar projection from the first guide slot into a retraction slot following plunger depression.
Figure 6C:
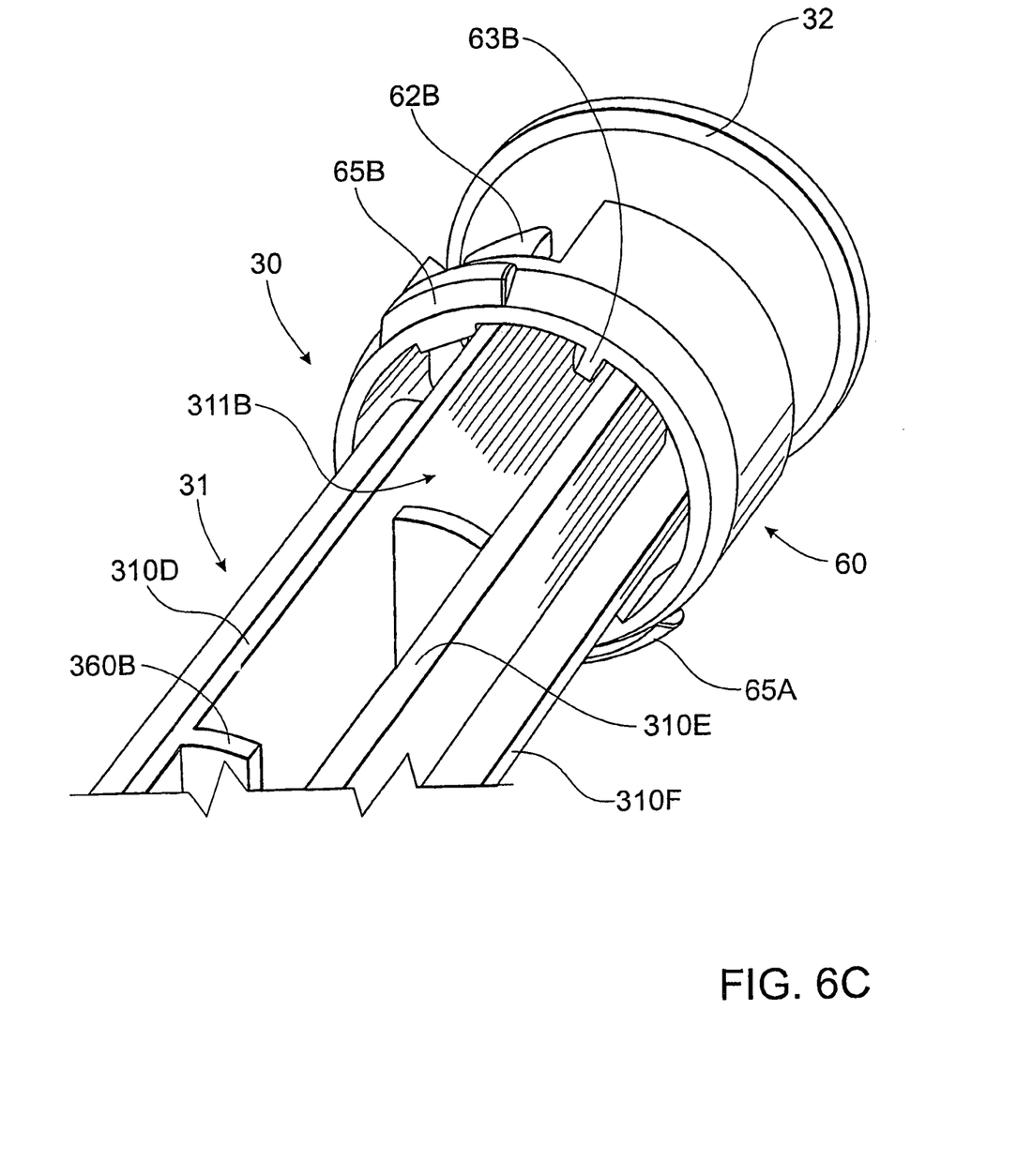
FIG. 6C shows a second collar projection in a second guide slot in the first plunger member.

Referring to FIG. 6A, B and C, during withdrawal of plunger 30 to fill barrel 20 with fluid, rib 63A of collar 60 is slidably located in first guide slot 311A of plunger rod 31 and rib 63B of collar is slidably located within second guide slot 311B (shown in FIG. 6C). This arrangement prevents rotation of plunger relative to collar 60 and needle mount 40 and maintains alignment of plunger means 340 for engaging needle mount 40 via plunger-engaging portions 44A, 44B of needle mount 40.

Withdrawal of plunger 30 is limited by abutment 360A in guide slot 311A bearing against rib 63A of collar 60 and abutment 360B in guide slot 311B bearing against rib 63B. The particular position of abutments 360A, 360B in respective guide slots 311A, 311B will therefore determine the length of travel of plunger 30 and hence the volume of fluid that is drawn into barrel 20. For example, FIG. 2 shows the location of abutment 360A for a 3 mL syringe; for a 5 mL syringe ledge 351A would act as abutment 360A.

At the end of plunger 30 withdrawal, the fluid contents of syringe 10 are delivered by depression of plunger 30.

At the end of delivery, there are three events that occur.

Firstly, needle mount 40 is disengaged from barrel insert 50 to allow retraction of needle mount 40 and needle 12.

Secondly, plunger rod 31 engages needle mount 40 via engaging means 340 to retract needle mount 40 and needle 12.

Thirdly, plunger rod 31 and seal member 33 are rotatably disengaged to allow decompression of spring 70, which drives retraction of plunger rod 31, needle mount 40 and needle 12 coupled therewith.

Figure 7A:
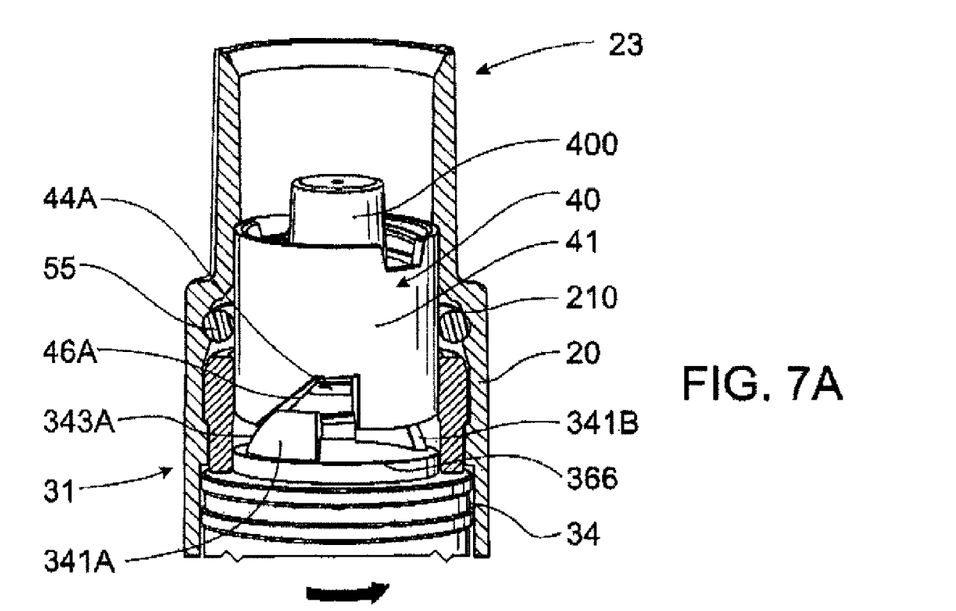
FIGS. 7A and 7B are sequential perspective views showing engagement between a first plunger member and a needle mount.
Figure 7B:
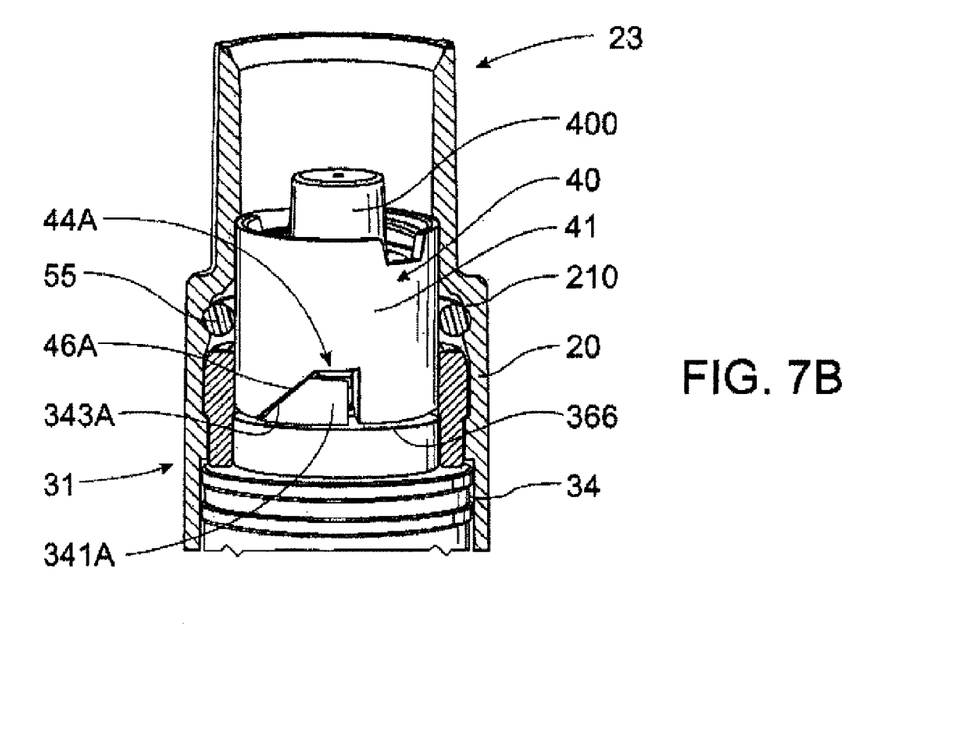

At the end of delivery, in order to release needle mount 40 from barrel 20, plunger lip 366 of plunger rod 31 forcibly displaces respective arms 53A, 53B of barrel insert 50 radially outwardly in the direction shown in FIG. 3, to thereby disengage grips 56A, 56B from base rim 43 of needle mount 40. This is accompanied by barbs 342A, 342B of plunger rod 31 engaging ledges 47A, 47B in needle mount 40 to thereby facilitate retraction of needle mount 40 by plunger 30, as shown in FIG. 7A and FIG. 7B.

Figure 8:
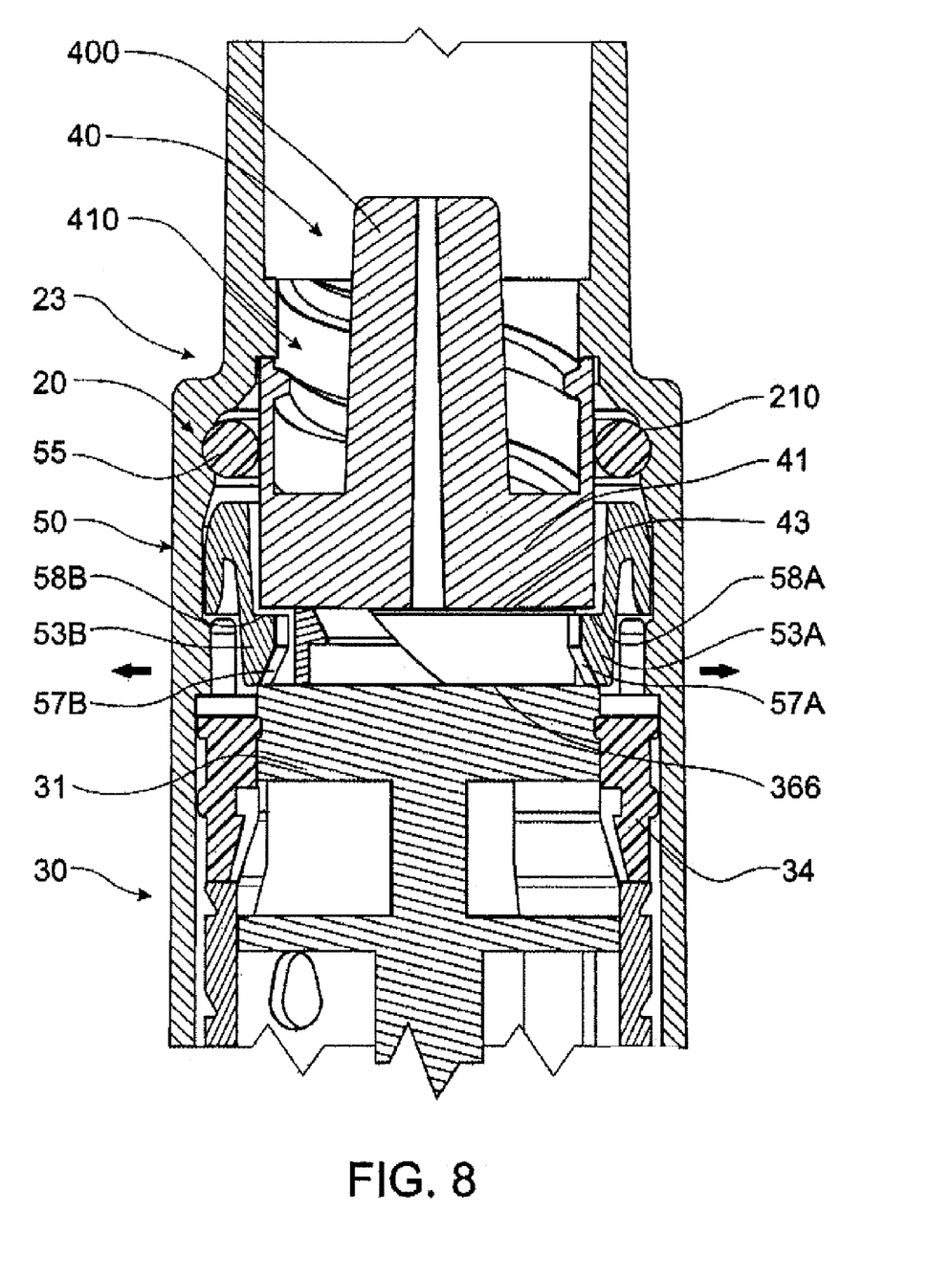
FIG. 8 is a sectional view of a first plunger member just prior to disengaging a barrel insert from a needle mount.
Figure 9:
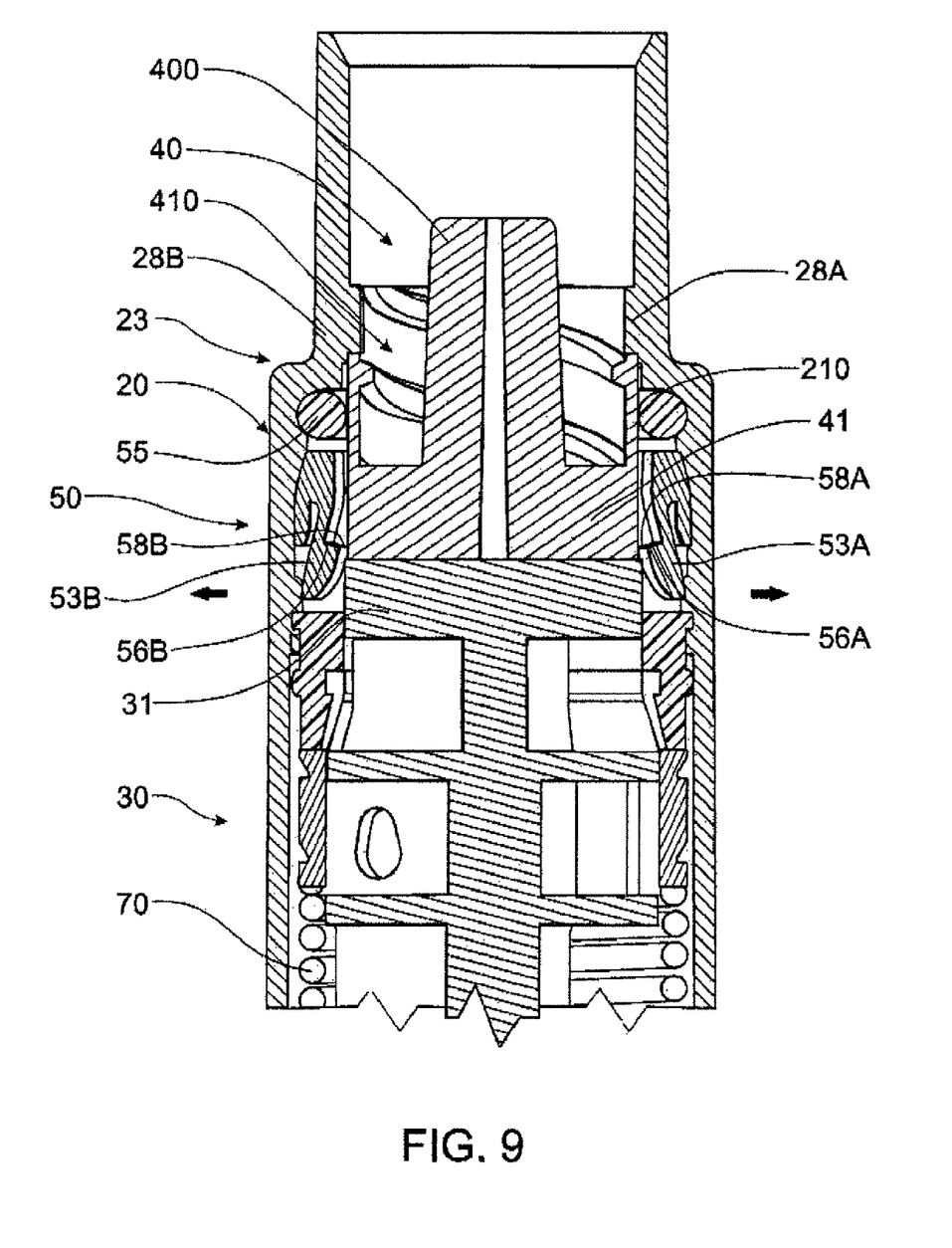
FIG. 9 is a sectional view of a first plunger member having disengaged a barrel insert from a needle mount.

As can be seen in FIG. 8 and FIG. 9, plunger lip 366 of plunger rod 31 spreads arms 53A, 53B of barrel insert 50 radially outwardly as indicated by the solid arrows. Angled faces 57A, 57B of arms 53A, 53B slide against plunger lip 366, causing barrel insert 50 to slide towards O-ring 55 after grips 56A, 56B of arms 53A, 53B have cleared base rim 43 of needle mount 40.

As best seen in FIG. 9, respective corners 58A, 58B of arms 53A, 53B come to rest on the outside of needle mount body 41 to permanently release the needle mount 40 and allow it to pass through barrel insert 50 and seal mount 33 with seal 34 which are retained at needle end 23 of barrel 20 by spring 70. At this location, barrel insert 50 can no longer retain a needle mount 40, thereby permanently disabling syringe 10 by preventing re-fitting of a needle mount 40.

Also evident in the embodiments shown in FIG. 8 and FIG. 9 is luer lock thread 410 in addition to luer 400. Alternatively, a luer slip (not shown) may be used.

As best seen in FIG. 7A, during engagement of respective plunger engaging means 44A, 44B in needle mount 40, by barbs 342A, 342B of plunger rod 31, inclined edges 343A, 343B of barbed arms 341A, 341B of plunger rod 31 bear against respective, complementary angled faces 46A, 46B on needle mount 40 which forces a slight rotation of plunger rod 31 relative to seal member 33 in the direction indicated by the arrow in FIG. 7A, which facilitates disengagement of bayonet coupling 300.

Disengagement of plunger rod 31 and seal mount 33 allows decompression of spring 70 which pushes against seal mount 33 and rims 330A, 330B on plunger rod 31 to thereby force retraction of plunger rod 31 together with needle mount 40 and needle 12 engaged therewith. Seal mount 33 and barrel insert 50 remain at needle end 23 of barrel 20.

Disengagement of plunger rod 31 from seal mount 33 allows decompression of spring 70 and retraction of plunger rod 31 with needle mount 40 and needle 12 attached thereto, followed by activation of disabling means 80 to prevent subsequent movement of plunger rod 31. When plunger rod 31 rotates just prior to retraction, rib 63A of collar 60 slidably moves through gate 312 from guide slot 311A into retraction space 313, as shown in FIG. 6B, which thereby allows plunger rod 31 to retract while aligning pawls 62A, 62B of collar 60 with steps 350A, 350B of plunger rod 31.

Referring to FIG. 6C, rib 63B of collar 60 is located within guide slot 311B, which allows restricted rotational movement of plunger rod 31 within vanes 310D and 310E and thus maintain alignment of pawls 62A, 62B with steps 35A, 350B on plunger rod 31.

Figure 10:
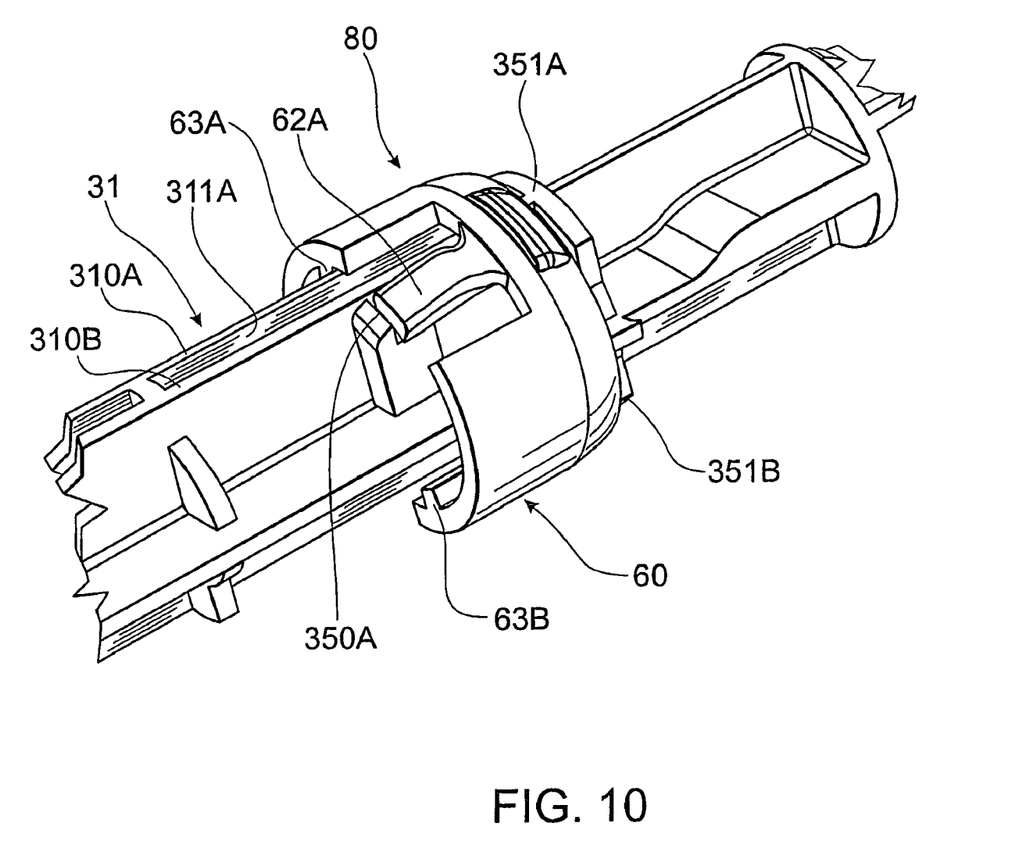
FIG. 10 is a perspective view of an embodiment of a disabling means.

Referring to FIG. 10, steps 350A, 350B are configured to allow travel of pawls 62A, 62B thereover as plunger rod 31 retracts, but to resist subsequent depression of plunger rod 31, by pawls 62A, 62B (not shown) bearing against steps 350A, 3501 (not shown) once disabling means 80 has been activated.

Also evident in FIG. 10 is that disabling means 80 prevents further withdrawal of plunger rod 31 by ribs 63A, 63B of collar 60 bearing against ledges 351A, 351B of plunger rod 31.

It should also be noted that following retraction of plunger rod 31 and needle mount 40, barrel insert 50, O-ring 55, seal mount 33 and seal 34 are urged toward needle end 23 of barrel 20 (not shown) by decompression of spring 70, thereby remaining at needle end 23 of barrel 20 and thus preventing refilling of barrel 20 from needle end 23.

It will be understood in light if the foregoing that the invention provides a robust, simple to operate automatically-disabling, single use syringe that prevents subsequent reuse and thereby minimizes the potential for disease transfer while also reducing the likelihood of needlestick injuries to the user.

Furthermore, the spring-driven retraction mechanism of the invention can accommodate a retraction spring that is compatible and effective with higher volume syringes, such as 3, 5 and even 10 mL syringes.

Throughout the specification, the aim has been to describe the preferred embodiments of the invention without limiting the invention to any one embodiment or specific collection of features. Various changes and modifications may be made to the embodiments described and illustrated without departing from the present invention.

The invention claimed is:

1. A plunger for a retractable syringe having a spring and a needle mount, said plunger comprising a first plunger member and a second plunger member that are releasably engaged during withdrawal and depression of said plunger to co-operatively maintain said spring in an initial compressed state, arranged so that rotational disengagement of said first plunger member and said second plunger member can facilitate decompression of said spring from the initial compressed state when required to force refraction of said first plunger member and said needle mount when engaged therewith, following depression of said plunger to deliver fluid contents of said syringe, wherein the second plunger member comprises a seal mounted thereto.

2. The plunger of claim 1, wherein the first plunger member and the second plunger member are releasably engageable by a bayonet coupling.

3. The plunger of claim 1 wherein said first plunger member is engageable with the needle mount to facilitate rotation of the first plunger member relative to the second plunger member.

4. The plunger of claim 1, wherein the first plunger member comprises a needle mount engagement device.

5. The plunger of claim 4, wherein the needle mount engagement device comprises two barbed arms.

6. A retractable syringe comprising a plunger, a barrel, a spring and a needle mount, said plunger comprising a first plunger member and a second plunger member that are releasably engaged during withdrawal and depression of said plunger to co-operatively maintain said spring in an initial compressed state and are rotationally disengageable to facilitate decompression of said spring to force retraction of said first plunger member and said needle mount, when engaged therewith, following depression of said plunger to deliver fluid contents of said syringe, wherein the second plunger member comprises a seal mounted thereto.

7. The retractable syringe of claim 6, wherein the first plunger member and the second plunger member are engaged by a bayonet coupling.

8. The retractable syringe of claim 6, wherein the first plunger member is engageable with the needle mount to facilitate rotation of the first plunger member relative to the second plunger member.

9. The retractable syringe of claim 6, wherein the first plunger member comprises a needle mount engagement device.

10. The retractable syringe of claim 9, wherein the needle mount engagement device comprises two barbed arms.

11. The retractable syringe of claim 10, wherein the needle mount comprises recesses that are respectively engageable by the barbed arms.

12. The retractable syringe of claim 6, further comprising a collar mounted to the barrel.

13. The retractable syringe of claim 12, wherein said collar comprises one or more projections capable of co-operating with one or more abutments of said first plunger member to form a plunger disabling device that is capable of preventing subsequent depression and/or withdrawal of said first plunger member following retraction of the needle mount.

14. The retractable syringe of claim 13, wherein the first plunger member comprises steps, and wherein the one or more projections comprise two pawls that are engageable with respective steps on said first plunger member to co-operably prevent subsequent depression said first plunger member following retraction of the needle mount and thereby prevent syringe re-use.

15. The retractable syringe of claim 13, wherein the first plunger member comprises ledges, and wherein the one or more projections comprise two ribs that are engageable with respective ledges on said first plunger member to co-operably prevent subsequent withdrawal of said first plunger member following retraction of the needle mount and thereby prevent syringe re-use.

16. A retractable syringe comprising:
a barrel;
a collar mounted to the barrel and comprising two ribs and two pawls;
a refraction spring;
a needle mount located at a needle end of the barrel; and
a plunger operably located in said barrel and engageable with said needle mount, said plunger comprising:
a first plunger member having two steps and two ledges; and
a second plunger member and a seal mounted thereto;
wherein the first plunger member and the second plunger member are releasably coupled during withdrawal and depression of said plunger to co-operatively maintain said spring in an initial compressed state and can subsequently be rotatably uncoupled to facilitate decompression of said spring to force retraction of said first plunger member and said needle mount when engaged therewith following depression of said plunger to deliver fluid contents of said syringe and wherein said two pawls are engageable with respective steps on said first plunger member to co-operably prevent subsequent depression said first plunger member and said two ribs are engageable with respective ledges on said first plunger member to co-operably prevent subsequent withdrawal of said first plunger member following retraction of the needle mount and a needle.

17. The syringe of claim 16, arranged so that following retraction of the first plunger member, the needle mount and the needle, said second plunger member and said seal remain at a needle end of the barrel thereby preventing refilling and re-use of the syringe.

18. A method of making a plunger for a syringe, the method comprising:
   releasably engaging a first plunger member and a second plunger member so that during withdrawal and depression of said plunger the first plunger member and the second plunger member co-operatively maintain a spring in an initial compressed state;
   arranging so that rotational disengagement of the first plunger member and the second plunger member decompresses the spring from the initial compressed state to force refraction of the first plunger member and a needle mount when engaged therewith, following depression of the plunger to deliver fluid contents of the syringe, wherein the second plunger member comprises a seal mounted thereto.

19. The method of claim 18, wherein the releasably engaging the first plunger member and the second plunger member further comprises releasably engaging the first plunger member and the second plunger member by a bayonet coupling.

20. The method of claim 18 wherein the arranging further comprises arranging the first plunger member to be disengaged from the second plunger member by the first plunger member engaging the needle mount to facilitate rotation of the first plunger member relative to the second plunger member.

21. The method of claim 18, wherein the first plunger member further comprises a needle mount engagement device.

22. The method of claim 18, wherein the needle mount engagement device comprises two barbed arms.

23. A method of making a retractable syringe, the method comprising:
   providing a plunger, a barrel, a spring and a needle mount;
   releasably engaging a first plunger member and a second plunger member so that during withdrawal and depression of said plunger the first plunger member and the second plunger member co-operatively maintain the spring in an initial compressed state; and
   arranging so that rotational disengagement of the first plunger member and the second plunger member decompresses the spring to force retraction of the first plunger member and the needle mount, when engaged therewith, following depression of the plunger to deliver fluid contents of the syringe, wherein the second plunger member further comprises a seal mounted thereto.

24. The method of claim 23, wherein the releasably engaging the first plunger member and the second plunger member further comprises releasably engageable the first plunger member and the second plunger member by a bayonet coupling.

25. The method of claim 23, wherein the arranging further comprises arranging the first plunger member to be disengaged from the second plunger member by the first plunger member engaging the needle mount to facilitate rotation of the first plunger member relative to the second plunger member.

26. The method of claim 23, wherein the first plunger member further comprises a needle mount engagement device.

27. The method of claim 26, wherein the needle mount engagement device comprises two barbed arms.

28. The method of claim 27, wherein the needle mount further comprises recesses that are respectively engageable by the barbed arms.

29. The method of claim 23, further comprising mounting a collar to the barrel.

30. The method of claim 29, wherein the collar comprises one or more projections capable of co-operating with one or more abutments of the first plunger member to form a plunger disabling device that is capable of preventing subsequent depression and/or withdrawal of the first plunger member following retraction of the needle mount.

31. The method of claim 30, wherein the one or more projections comprise two pawls that are engageable with respective steps on the first plunger member to co-operably prevent subsequent depression the first plunger member following retraction of the needle mount and prevent syringe re-use.

32. The method of claim 30, wherein the one or more projections comprise two ribs that are engageable with respective ledges on the first plunger member to co-operably prevent subsequent withdrawal of the first plunger member following retraction of the needle mount and prevent syringe re-use.

* * * * *